Figure 1:
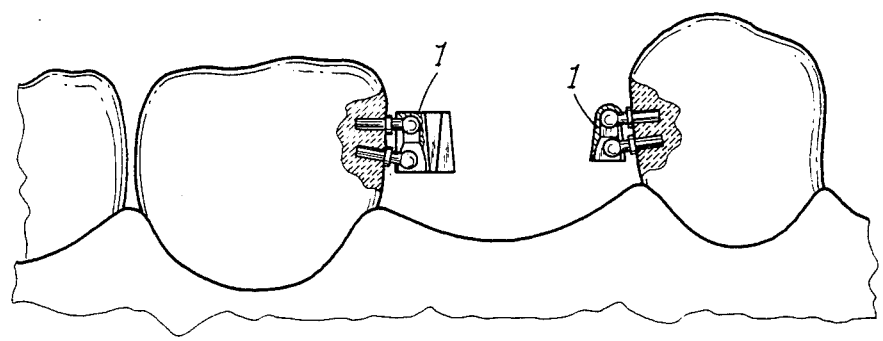

United States Patent [19]

Hader

[11] Patent Number: 4,556,388
[45] Date of Patent: Dec. 3, 1985

[54] DENTAL ATTACHMENT FOR FIXING DENTAL PROSTHESES

[76] Inventor: Helmut Hader, Les Allées 25, CH - 2300 La Chaux-De-Fonds, Switzerland

[21] Appl. No.: 471,675

[22] Filed: Mar. 3, 1983

[30] Foreign Application Priority Data

Mar. 31, 1982 [CH] Switzerland .................. 1976/82

[51] Int. Cl.$^4$ ............................................. A61C 13/22
[52] U.S. Cl. .................................................. 433/181
[58] Field of Search .............. 433/181, 182, 183, 205

[56] References Cited

FOREIGN PATENT DOCUMENTS 619856  3/1980  Switzerland .................. 433/182
2085303  4/1982  United Kingdom ............ 433/181

Primary Examiner—Robert Peshock
Attorney, Agent, or Firm—Young & Thompson

[57] ABSTRACT

A dental attachment for fixing a dental prosthesis to healthy teeth comprising a male portion 1 which is rigidly fixed to a healthy tooth and a female portion 2 which is rigidly fixed to the dental prosthesis, the male portion 1 comprising two independent pins 7 which are intended to be engaged and sealed in a hole formed in a living tooth, and which have a spherical head 8, and the male portion further comprises a coupling portion 3 having an opening 5 which opens at a lower face and by way of an aperture 6 at its lateral face, the assembly being so arranged that the spherical coupling heads 8 of the pins 7 may be housed and sealed in the opening 5, the pins 7 extending from the coupling portion 3 through said aperture 6, the female portion 2 then being connected to the male portion 1.

10 Claims, 7 Drawing Figures

U.S. Patent  Dec. 3, 1985  4,556,388

DENTAL ATTACHMENT FOR FIXING DENTAL PROSTHESES

The present invention relates to an attachment for fixing dental prostheses.

The arrangements used hitherto for fixing dental prostheses require crowns to be fitted on to the healthy teeth on each side of the gap to be filled, to permit bridges and even partial dentures to be fixed on to the crowns. That procedure involves cutting healthy teeth which serve to carry the dental prostheses, thus making them much more vulnerable to infection and decay. It will be appreciated that that is not desirable, and systems have been developed, such as that described in Swiss Pat. No. 619,856, which use anchoring members comprising two teat elements which are intended to be fixed in a healthy tooth and which serve to carry a screwthreaded rod on to which are screwed studs which serve for fixing the prostheses.

That arrangement is not satisfactory because it is necessary to drill two strictly parallel cavities to receive the test elements, and that cannot be achieved under pratical conditions. In fact, this arrangement also involves the necessity for forming substantial openings in the healthy teeth serving to carry the anchoring means, in order to be able to secure them in the required position. In addition, the use of irremovable screwthreaded rods cause problems for the user, particularly when fixing removable units.

According to the present invention there is provided a dental attachment for fixing dental prostheses to healthy teeth, comprising a male portion which can be rigidly fixed to a healthy tooth and a female portion which is rigidly fixed to the dental prostheses, the male portion comprising two independent pins which are intended to be secured by one of their ends in a healthy tooth and which have at their other end a spherical head, and said male portion also comprising a coupling member having a cavity or opening which opens at a lower face and also by way of an aperture in its lateral face, the assembly being so arranged that the spherical coupling members of the pins may be housed and sealed in the cavity or opening, the pins extending from the connecting member through said aperture.

Figure 2:
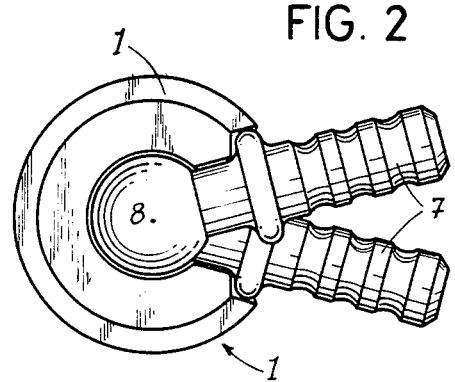
Figure 4:
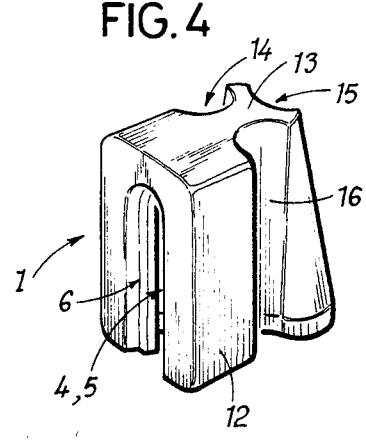
Figure 3:
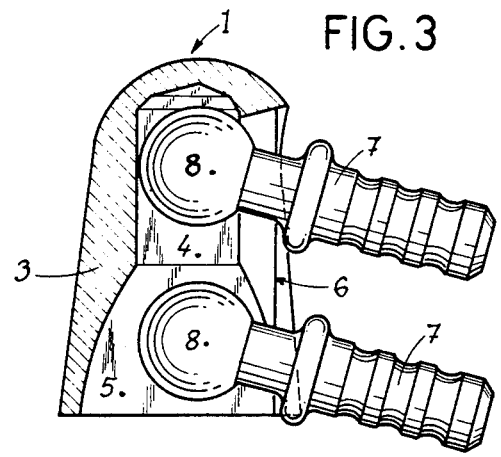
Figure 5:
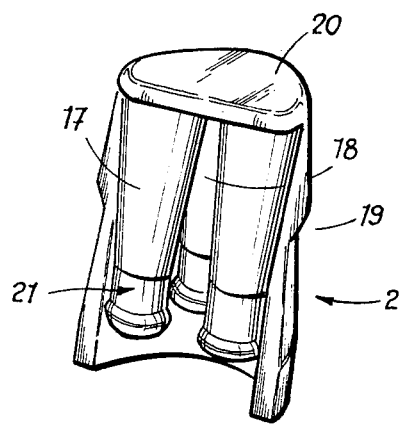
Figure 6:
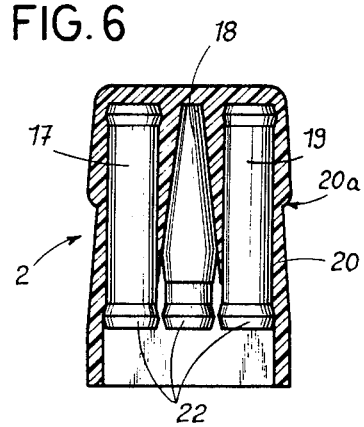
Figure 7:
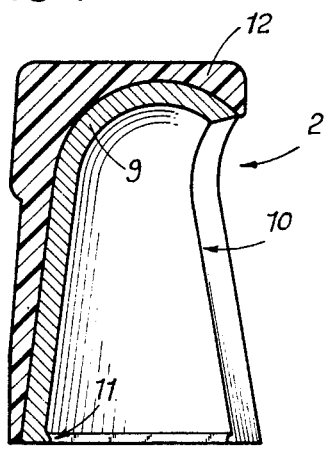

Two embodiments of the invention will now be described, by way of examples, with reference to the accompanying drawings, in which:

FIG. 1 shows two healthy teeth each provided with the male portion of a dental attachment according to the present invention, the one shown on the right hand tooth constituting a first embodiment and the one shown on the left hand tooth constituting a second embodiment, FIG. 2 is a plan view of the first embodiment of the male portion of the attachment, FIG. 3 is a partly sectional side view of the male portion illustrated in FIG. 2, FIG. 4 is a perspective view of part of a second embodiment of the male portion, FIG. 5 is a perspective view of the female portion of the attachment for co-operating with the male portion shown in FIG. 4, FIG. 6 is a cross-sectional view of the female portion illustrated in FIG. 5, and FIG. 7 is a cross-sectonal view of a female portion for co-operating with the male portion illustrated in FIGS. 2 and 3.

The attachment illustrated in the drawings comprises a male portion 1 which is intended to be fixed in a healthy tooth, and a female portion 2 which is intended to be incorporated in/or attached to a dental prostheses.

In the embodiment illustrated in FIGS. 1, 2, 3 and 7, the male portion 1 comprises a body 3 having a substantially conical outside surface and a rounded upper part, the body 3 flaring outwardly from the rounded upper part to its bottom end. The body 3 is provided with a cavity or opening having a cylindrical upper part 4 and a downwardly open, flared, lower part 5. A lateral aperture 6 provides access to the opening 4, 5, at the side of the body 3.

The male portion 1 further comprises two pegs or pins 7 having a spherical head 8 intended to be positioned in the opening 4, 5, the diameter of the head 8 being larger than the width of the aperture 6.

The free end of each of the pins 7 is intended to be sealed in a respective hole drilled in a healthy tooth.

The pins 7 are displaceable angularly and axially with respect to each other, the heads 8 thereof always remaining in the opening 4, 5 and thus engaged with respect to the body 3.

By virtue of this arrangement, the dentist can drill two small holes or recesses, the dimensions of which correspond to those of the pins 7, in a healthy tooth, for receiving the pins 7. The holes or recesses drilled in the tooth may be small in size and do not necessarily have to be parallel to each other nor spaced at a predetermined distance. In fact, as the pins 7 are movable with a translatory movement and with an angular movement, they can be easily fitted into the two drillings and then sealed therein. The opening 4, 5 is also fitted with a sealing material when the body 3 is correctly oriented to permit the prosthesis to be fixed in position.

The corresponding female portion 2 (FIG. 7) is formed by a conical cap member 9, the internal shape of which corresponds to the external shape of the conical body 3, and which has a side aperture 10. The cap 9 can thus be fitted over the conical body 3, once the body 3 has been fixed to a tooth in the mouth, as described hereinbefore, by means of the pins 7.

The conical cap 9 has a lower lip portion 11 which co-operates with the lower edge of the conical body 3 to lock the cap 9 on the body 3 in the engaged position of use.

The cap 9 may be made of a slightly elastic material such as a plastics material.

The female portion 2 is incorporated in the dental prosthesis 12 by any known means.

In the second embodiment illustrated in FIGS. 1, 4, 5 and 6, the male portion 1 comprises a body 12 which also has a cavity or opening 4, 5 which is accessible through the rear side of the body 12 by way of an aperture 6 and which is inteded to receive the spherical heads 8 of two pins 7.

The body 12 of the male portion 1 also has a coupling portion 13 having three conical millings or drillings 14, 15, 16 with their axes parallel. The conical drillings 14, 15 and 16 flare outwardly towards the upper face of the body 12 of the male portion 1.

The coupling portion 13 is intended to co-operate with a female portion 2 of the attachment, as illustrated in FIGS. 5 and 6, which comprises three pins 17, 18 and 19 mounted in a mass of plastics material 20, with an aperture 21.

The pins 17, 18 and 19 are also conical and flare outwardly in an upward direction, and at their lower end are provided with a retaining lip or catch means 22.

The female portion 12 is intended to be incorporated in a dental prosthesis. That may be effected for example by providing in the dental prosthesis, a cavity or opening which corresponds to the form of the mass of plastics material 20 of the female portion 2. The female portion 2 is then received in the manner of a press-stud in the cavity or opening in the dental prosthesis. It is retained in position in the prosthesis by a shoulder 20a co-operating with the walls of the cavity or opening formed in the dental prosthesis.

To fix the dental prosthesis, it is sufficient to engage the pins 17, 18 and 19 in the drillings 14, 15 and 16, which is extremely simple because of the conical configuration of the pins and the drillings. By pushing the pins right home into the drillings, the retaining lip portion 22 is moved into a position under the coupling portion 13 and holds the female and male portions 1 and 2 in the coupled position.

This attachment is particularly attractive for the following reason:

1. The interference with the healthy teeth serving as a carrier is minimised, as the drillings may be small and the position thereof is not critical, as also is the case with their orientation.

2. The dental prosthesis may be removably fixed.

3. The alignment of the two or more male portions serving to fix the prosthesis, and likewise in regard to the female portion, is not a critical consideration, by virtue of the tapered configuration of the drillings and the pins respectively of the body and the cap, as well as the elasticity of the mass of plastics material of the female portion, which permit the portions automatically to assume their proper positions when the prosthesis is set in place.

4. It can be manufactured on a mass-production basis, and the cost price thereof can be kept very low.

I claim:

1. A dental attachment for fixing dental prosthesis to healthy teeth, comprising a male portion which can be rigidly fixed to a healthy tooth and a female portion which is rigidly fixed to the dental prostheses, the male portion comprising two independent pins which are intended to be secured by one of their ends in a healthy tooth and which have at their other end a spherical head, and said male portion also comprising a coupling member having a cavity or opening which opens at a lower face and also by way of an aperture in its lateral face, the assembly being so arranged that the spherical coupling members of the pins may be housed and sealed in the cavity or opening, the pins extending from the connecting member through said aperture.

2. A dental attachment as claimed in claim 1, in which the coupling member has three frustoconical drillings with their axes parallel, the drillings flaring outwardly upwardly and being disposed in the triangular configuration.

3. A dental attachment as claimed in claim 1, in which that the coupling member comprises a conical body, the upper end of which is rounded and whose outer surface flares outwardly in a downwardly direction.

4. A dental attachment as claimed in claim 2, in which the female portion comprises three conical pins which are partially embedded within a mass of plastics material, said three pins having their axes parallel and being disposed in a triangular configuration, the mass of plastics material having an aperture permitting the pins to be engaged with the frustoconical drillings of the coupling member of the male portion.

5. A dental attachment as claimed in claim 4, in which the lower end of each of the three pins has a locking catch means or lip which co-operates with the lower edge of the coupling member of the male portion.

6. A dental attachment as claimed in claim 3, in which the female portion is formed by a conical cap member having an aperture for receiving the conical body of the coupling member.

7. A dental attachment as claimed in claim 6, in which the lower end of the cap member has a locking lip or catch means which co-operates with the lower edge of the conical body of the coupling member.

8. A female portion of an attachment as claimed in claim 1, comprising three conical pins which are partially embedded within a mass of plastics material, said three pins having their axes parallel and being disposed in a triangular configuration, the mass of plastics material having an aperture permitting the pins to be engaged in drillings of a coupling member.

9. A female portion as claimed in claim 8, in which the lower end of the pins has a locking catch or lip means.

10. A female portion as claimed in claim 8, fixed in dental prosthesis on the press-stud principle, the mass of plastics material of said female portion constituting the male portion of said press-stud type coupling.

* * * * *